United States Patent
Fredlund et al.

(10) Patent No.: US 9,574,997 B2
(45) Date of Patent: Feb. 21, 2017

(54) METHOD FOR CLASSIFYING SEEDS, COMPRISING THE USAGE OF INFRARED SPECTROSCOPY

(75) Inventors: Bo Kenneth Fredlund, Landskrona (SE); Johan Sander, Landskrona (SE)

(73) Assignee: Syngenta Participations AG, Basel (CH)

( * ) Notice: Subject to any disclaimer, the term of this patent is extended or adjusted under 35 U.S.C. 154(b) by 163 days.

(21) Appl. No.: 13/879,588

(22) PCT Filed: Oct. 14, 2011

(86) PCT No.: PCT/EP2011/005176
§ 371 (c)(1),
(2), (4) Date: May 20, 2013

(87) PCT Pub. No.: WO2012/048897
PCT Pub. Date: Apr. 19, 2012

(65) Prior Publication Data
US 2013/0229647 A1  Sep. 5, 2013

(30) Foreign Application Priority Data
Oct. 15, 2010 (EP) .................................. 10013708

(51) Int. Cl.
*B07C 5/34* (2006.01)
*G01N 21/55* (2014.01)
(Continued)

(52) U.S. Cl.
CPC ............ *G01N 21/55* (2013.01); *B07C 5/3425* (2013.01); *G01N 21/3563* (2013.01); *G01N 21/359* (2013.01); *G01N 21/3581* (2013.01)

(58) Field of Classification Search
CPC .... B07C 5/3425; B07C 5/3427; G01N 21/359
(Continued)

(56) References Cited

U.S. PATENT DOCUMENTS 3,044,619 A   7/1962  Knolle
6,080,950 A   6/2000  Jalink
(Continued)

FOREIGN PATENT DOCUMENTS

GB   670461   4/1952
GB   776292   6/1957
(Continued)

OTHER PUBLICATIONS

Tigabu, Mulualem et al: "Simultaneous detection of filled, empty and insect-infested seeds of three Larix species with single seed near-infrared transmittance spectroscopy", New Forests 27, 2004, pp. 39-53.*

(Continued)

*Primary Examiner* — Jeremy R Severson
(74) *Attorney, Agent, or Firm* — Yoshimi D. Barron

(57) ABSTRACT

A method for classifying sugar beet seeds, comprising the steps of measuring an IR-spectrum of each seed, preferably sugar beet seeds, classifying seeds according to their IR-spectrum, wherein the seed-class differs from other seed-classes by a quality of composition, wherein said quality of composition is reflected in a specific IR-spectrum. In one embodiment the seeds are sorted according to their classification by a sorting means.

5 Claims, 8 Drawing Sheets

(51) Int. Cl.
*B07C 5/342* (2006.01)
*G01N 21/3563* (2014.01)
*G01N 21/3581* (2014.01)
*G01N 21/359* (2014.01)

(58) Field of Classification Search
USPC ............... 209/577, 587; 250/341.8; 356/51
See application file for complete search history.

(56) References Cited

U.S. PATENT DOCUMENTS

| | | |
|---|---|---|
| 2003/0177525 A1 | 9/2003 | Fender et al. |
| 2004/0055211 A1 | 3/2004 | Lestander |

FOREIGN PATENT DOCUMENTS

| | | |
|---|---|---|
| GB | 2195877 | 4/1988 |
| JP | 7260682 | 10/1995 |
| JP | 11051860 | 2/1999 |
| WO | 2009/118111 | 10/2009 |
| WO | 2010/000266 | 1/2010 |
| WO | WO 2012149398 A1 * | 11/2012 |

OTHER PUBLICATIONS

International Search Report, International Application No. PCT/EP2011/005176, completion date: Jan. 17, 2012.

Tigabu M et al: "Discrimination of viable and empty seeds of Pinus patula Schiede & Deppe with near-infrared spectroscopy", New Forests May 2003 Kluwer Academic Publishers NL, vol. 25, No. 3, May 2003, pp. 163-176.

Yuji Nukasa et al: "Application of Near-Infrared Diffuse Reflectance Spectroscopic Analysis for Estimating the Ratio of True Seed Weight to Fruit Weight in Sugar Beet Seed", Plant Production Science, vol. 8, No. 1, Jan. 1, 2005, pp. 3-7.

Maisl M et al: "Process Monitoring using Three Dimensional Computed Tomography and Automatic Image Processing", Internet Citation, Sep. 27, 2006, pp. 1-6.

* cited by examiner

METHOD FOR CLASSIFYING SEEDS, COMPRISING THE USAGE OF INFRARED SPECTROSCOPY

This application is a 371 of International Application No. PCT/EP2011/005176 filed Oct. 14, 2011, which claims priority to EP 10013708.2 filed Oct. 15, 2010, the contents of which are incorporated herein by reference.

BACKGROUND OF THE INVENTION

The present invention refers to a method for classifying seeds, in particular sugar-beet seeds, by the use of infrared-spectroscopy. One focus of the classification is an improvement of the seed quality characteristics, in particular the field emergence characteristics of sugar-beet seeds.

Sugar-beet is a cultivated plant of *Beta vulgaris* which is a plant whose root contains a high concentration of sucrose. It is grown commercially for sugar production. The sugar comes from the taproot of the beetroot plant, chard and fodder beet, all descended by cultivation from the sea beet. Beet sugar accounts for 30% of the world's sugar production.

The flowering habit of sugar beet leads to a very heterogeneous mix of seed quality in the harvested ready seed (i.e., raw seed). One example of a seed quality that needs to be controlled in order to meet market requirements and that requires a strict selection of the seeds having a certain quality is, for example, field emergence performance.

Despite the likeness of the seeds from the outside they do not form a homogeneous fraction but are quite different in their characteristics, such as, for example, field emergence characteristics which is a collective name for features like viability (i.e., final population at normal field-conditions), growth-rate (i.e., speed of early emergence) and vigour (i.e., final population at stressed field-conditions). The result of the heterogeneity in field emergence characteristics in a seed lot could be loss of harvest, reduction of sugar-beet quality due to heterogeneous root size and unpredictability of expected crop yield.

For example the early emergence of a seed can occur after about 50-60 day degrees, but on average the first emergence appear after about 80 to 110 day degrees in a normal population. However, several seed will not emerge at all, i.e., no sugar beet plants will grow.

One reason for these differences in field emergence characteristics of sugar beet seeds are abnormal seeds, like empty seeds, twin-embryos or seeds with free space(s) inside or partially filled seeds which account for the heterogeneity of the natural seed fractions.

Since said quality-differences are nearly impossible to deduce from the outside, due to the fact that the sugar beet seed is hidden inside a fruit wall, classification and/or sorting are difficult to perform.

In commercial seed production therefore the problem arises, that only a fraction of the seeds shows the desired field emergence characteristics. It is not unlikely that up to 70% of the raw seed from a production does not show a certain seed quality, like for example field emergence characteristics, and need to be discarded.

Therefore, it would be a great improvement in terms of productivity and cost/value ratio, if the percentage of seeds which show the desired field emergence characteristics could be increased in commercial seeds.

In the prior art different techniques for seed characterisation and/or sorting have been developed.

Mukasa et al., Plant Prod. Sci. 8 (1): 3-7 (2005) evaluates the water content and true weight of sugar-beet seeds by NIR. However, this method is a rather imprecise technique and has been shown to be inappropriate to predict seed quality characteristics.

Soltani, A., Improvement of Seed Germination of *Fagus orientalis* Lipsky. ISSN 1401-6230, ISBN 91-576-6509-5 describes the improvement of seed germination of oriental beech by NIR-analysis. However, again the author focused only on one particular aspect of the seeds, namely their germination characteristic. Complex characteristics, such as field emergence characteristics, have not been disclosed.

Mittler et al., "Hohe Saatgutqualität für leistungsfähige Bestände", Zuckerrübe 2004, Vol. 53 evaluates the quality of seeds with X-ray techniques. However, the classification of seeds with X-ray is time-consuming, expensive and difficult to automate.

EP 1 578 544 B1 describes sorting means to sort "objects" and "granules", as for example plastic parts, pills, beads, grains, beans and the like. Sorting for complex characteristics, such as field emergence characteristics, have not been disclosed.

EP 1 401 589 B1 describes sorting means to sort objects comprising organic material. Sorting for characteristics, such as field emergence characteristics, have not been disclosed.

Dowell et al., Cereal Chem. 83 (5):537-543, Dowell et al., Cereal Chem. 86(5):527-533 and Tønning et al., Cereal Chem. 86(6):706-713 use sorting means for post-harvest quality control and/or improvement with respect to further processing of different crop, primarily wheat or other cereals.

US 2004/0055211 uses a method for determining viability or non-viability of seeds from *Pinus sylvestris* L. Methods for discriminating different complex seed qualities within the fraction of viable seeds are not disclosed. Tigabu and Odén (New Forests (2003) 25: 163-176) use a method to discriminate between viable and empty seeds of *Pinus patula*. Again, methods for discriminating between different complex seed qualities within the fraction of viable seeds are not disclosed.

WO 2010/000266 also discloses a method for discriminating between viable and non-viable seeds. Seeds are sorted according to categories like "filled, but dead", "infested", "infected", "empty", or the like (cf. p. 15, lines 17-19). Also in this publication no methods for discriminating different complex seed qualities within the fraction of viable seeds are disclosed.

Thus, the prior art methods do not allow to sort for seeds based on complex quality characteristics. Especially methods for discriminating different complex seed qualities of viable seeds are not disclosed.

In view of the above, one object of the invention was to find a method which allows for both fast and cheap analysis of the seeds as well as a sufficiently accurate classification of viable seeds according to complex quality characteristics, such as field emergence characteristics.

The present invention solves this problem.

SUMMARY OF THE INVENTION

According to one aspect, the present invention relates to a method for classifying seeds, comprising the steps of
 a. measuring an IR-spectrum of the seeds,
 b. classifying seeds according to their IR-spectrum yielding at least two seed classes, wherein the first seed-class differs from the at least one other seed-class by a quality of composition, wherein said quality of composition is reflected in a specific IR-spectrum.

In another embodiment a method for classifying sugar-beet seeds is disclosed, comprising the steps of
a. measuring an IR-spectrum of each seed,
b. classifying seeds according to their IR-spectrum yielding at least two seed classes,
wherein the first seed-class differs from the at least one other seed-class by a quality of composition,
wherein the quality of composition is the functional quality of "field emergence characteristic" present in the sugar beet seed, and
wherein said quality of composition is reflected in a specific IR-spectrum.

The term "reflected in a specific IR-spectrum" refers both to a direct or indirect correlation between the IR-spectrum and the quality of composition.

In one embodiment an IR-spectrum of each single seed is measured and then classified according to the correlation of the IR-spectrum with different seed quality characteristics, such as "field emergence". In one embodiment a chemical quality may be measured directly with an IR-spectrometer resulting in a specific IR-spectrum reflecting the chemical quality. In another embodiment a sensoric quality may be not measured directly with an IR-spectrometer. However, if the chemical quality is correlated with the sensoric quality and the specific IR-spectrum is correlated with the chemical quality, the specific IR-spectrum is also correlated with the sensoric quality. Therefore, also the sensoric quality is reflected in a specific IR-spectrum. In another embodiment said correlation exists between other qualities of composition for example structural qualities, such as e.g. "free space", and functional qualities, such as e.g. "field emergence characteristics".

In one embodiment said method comprises the further step of sorting said classes of seeds yielding at least two sorted fractions of seeds which respectively differ from each other by a quality of composition, wherein said quality of composition is reflected in a specific IR-spectrum.

In one embodiment, the specific IR-spectrum is used to differentiate between different classes of seeds.

In one embodiment said method is applied to sugar beet seeds. As used herein, the term "sugar beet" refers to all species and subspecies within the genus *Beta* as well as to all kinds of cultivated beets of *Beta vulgaris* at any stage of development. Cultivated beets have been separated into four groups: leaf beet, garden beet, fodder beet and sugar beet. "Sugar beet" refers also to all cultivated beets including those grown for other purposes than the production of sugar, such as ethanol, plastics or other industrial products. In particular, "sugar beet" refers to fodder beet and sugar beet, but especially to sugar beet. The term "sugar beet" also includes sugar beet plants adapted for growth in tropical or subtropical regions.

The term "cultivated" with respect to the sugar beet plants means any sugar beet plant that are commercially grown for their production. The term "cultivated sugar beet plant" includes those plants which has been brought into cultivation and have been selectively bred for growing purposes.

In a further embodiment said quality of composition is selected from the group consisting of a chemical quality, a structural quality, a sensoric quality or a functional quality and/or a combination of one or more thereof. In one embodiment said structural quality is the percentage of "free space" present in the sugar beet seed.

In one embodiment said quality of composition refers to qualities important for sowing and development of the seed on the field, which is improved with respect to a seed composition not classified and/or sorted.

The term "chemical quality" encompasses any chemical quality relevant for and/or present in seeds. By way of examples the following qualities are to be mentioned: water content, fat content, sugar content, protein content, minerals content, content of certain functional groups, e.g. a alkyl-, alkenyl-, alkynyl-, phenyl-, benzyl-group, hydroxyl-, carbonyl-, aldehyde-, carbonate-, carboxylate-, carboxylic acid-, ether-, ester-, methyl-, ethyl- and/or ketone-group; a content of certain chemical bonds, e.g. peptide- and/or di-sulfide-bonds and/or any combination thereof.

The term "structural quality" encompasses any quality related to the inner and/or outer structure of the seeds. By way of examples the following qualities are to be mentioned: total diameter, that is the seed diameter including the fruit wall, total diameter without the fruit wall, true seed diameter, total volume including the fruit wall, part of the pericarp within the fruit wall, part of the hard torso within the fruit wall, part of true seed with respect to other seed structures, part of the free space with respect to other seed structures, part of the fruit wall with respect to other seed structures, part of the fruit wall cavity with respect to other seed structures and/or any combination thereof. In one embodiment the "free space part" is of particular interest since it is correlated with other qualities of the seed, in particular chemical and functional qualities.

The term "true seed" refers herein to plumule, perisperm and radicle together (cf. FIG. 8, (1), (4) and (5)). The "fruit wall" (cf. FIG. 8, (2)) refers herein to the pericarp and the hard torso together. The term "fruit wall cavity" is the inner part of the fruit wall which surrounds the "true seed" and in some cases surrounds also the "free space part" which is explained elsewhere in more detail. The "fruit cap" is also called "operculum" (cf. FIG. 8, (3)).

The term "sensoric quality" encompasses any quality of the seeds relating taste and/or smell. Examples for such "sensoric qualities" are salty taste, sweet taste and/or smell, less bitter taste and/or smell, complex taste and/or smell quality. In another embodiment the term "sensoric quality" refers to the sensoric quality of the final "fruit".

The term "functional quality" refers to any feature of the seeds relating to the functioning of the seed. The term comprises characteristics such as field emergence characteristics and/or potential of the seeds to produce "fruits", in particular sugar beet taproots, of desired quality in terms of, for example, sugar yield, sugar quality and/or simplified post-production.

The term "field emergence characteristic" refers to any feature of the seeds relevant for its performance in the field, i.e. after being sowed, such as viability (i.e., final population at normal field-conditions), growth-rate (i.e., speed of early emergence) and vigour (i.e., final population at stressed field-conditions).

In one embodiment the quality of "field emergence characteristic" defines different subsets of viable sugar beet seeds.

In another embodiment the quality of "field emergence characteristic" correlates with the composition is the structural quality of "free space" present in the sugar beet seed.

In another embodiment the sugar beet seed is classified according to one of the classes "no free space", "free space 1", "free space 2" and "free space 3" of the "free space" present in the sugar beet seed.

In another embodiment the sugar beet seed is classified according to one of the classes "no free space", "free space 1", "free space 2", "free space 3", "empty abnormal", "twin" and "part empty moon".

The term "stressed field-conditions" refers to conditions when the seed is planted early in the year and therefore the seed is stressed by cold weather conditions or even ground frost.

In one embodiment the classification is directed to a functional quality, for example an improvement of the field emergence characteristics. In this case, the improvement of the quality of the composition is an improvement of the field emergence characteristics of the composition. In some embodiments the improvement of the field emergence characteristics is an improvement in one or more of the characteristics selected from the group comprising viability, growth-rate and/or vigour.

In yet a further embodiment the mode of measurement of the IR-spectrum comprises reflectance or transmission, or both. In further embodiments for seeds of irregular shape, the seed is measured placing the seed so that the shortest diameter is parallel to the sensor beam and the longest diameter of the seed is perpendicular to the sensor beam.

In one embodiment the IR-spectrum is either near infra-red (NIR) defined herein as a frequency range from 120 to 400 THz and/or a wavelength of 2,700 to 750 nm, respectively. In another embodiment mid infra-red (MIR) is used. MIR is defined herein as a frequency range from 30 to 120 THz and/or a wavelength of 10 to 2.7 µm, respectively. In an even further embodiment far infra-red (FIR) is defined herein as a frequency range from 300 GHz to 30 THz and/or a wavelength of 1 µm to 10 µm, respectively. In a further embodiment NIR, MIR and/or FIR are combined for measurements.

In further embodiments a certain region of the IR-spectrum is chosen for measuring. In one embodiment wavelengths of 800 to 2700 nm, or 1000 to 2000 nm, or 1100 to 1500 nm, or 950 to 2040 nm or 1060 to 2380 nm or combinations thereof are chosen for classification.

The IR-region may be chosen according to the number of different classes desired. For example in one embodiment the NIR-spectrum between wavelengths of 950 to 2040 nm is used for a 5-class-classification. In another embodiment the wavelengths of 1060 to 2380 nm are used for a 3-class-classification.

In other embodiments also more broad or more narrow spectral regions and/or single peaks may be chosen, depending on the individual IR-characteristics of the seeds and the quality of sorting intended.

In further embodiments the IR-spectrum is filtered before classification. In one embodiment the filter is the application of a derivative of the spectrum, in particular the 1st, 2nd or 3rd derivative of the spectrum is used. In a further embodiment a smoothing filter is applied to the spectrum and/or one or more of the derivatives. In one embodiment the smoothing filter is a Savitzky-Golay smoothing filter.

In further embodiments the classification of the IR-spectrum is performed by a computer. In one embodiment a self-learning algorithm is used for classification. In some embodiments one or more of the following methods is used for classification of the data selected from the group comprising discriminant PLS (PLS-DA), Fischer discrimination, k nearest neighbours (kNN), artificial neural networks, SIMCA and/or support vector machines (SVM).

In one embodiment support vector machines are used for classification of the IR-spectra.

This invention also refers to the use of a sorting means for sorting seeds according to the method mentioned before. In some embodiments the seeds are sugar beet seeds. In some embodiments the seeds are individually measured, classified and individually sorted by the sorting means.

This invention also refers to a method of sorting seeds by using a sorting means. It is important to note, that in some embodiments an individual sorting of each seed is envisaged comprising the steps of individual IR-measurement, individual classification and individual sorting of the seed. In one embodiment a sorting means is used which is capable to perform a sorting according to the classification scheme calculated from the IR-spectra. Thus, in one embodiment the seeds, in particular sugar beet seeds, are sorted by the quality of composition of said seeds which is reflected in a specific IR-spectrum and wherein the quality of composition is selected from the group comprising a chemical quality, a structural quality, a sensoric quality or a functional quality or a combination of one or more thereof.

In one embodiment, said sorting means is selected from the group comprising a sorting apparatus, a gravitational sorter, a rotational sorter, a sieve-sorter, an optical sorter and/or a sorting machine comprising air-flow systems for separation of seed, wherein the sorting means is configured to run according to said method.

In one embodiment the sorting means comprises a rotating indented cylinder, wherein the seeds in the indented pockets are inspected by the IR-sensor and the seeds are pushed into different fractions according to their classification by compressed air.

In a further embodiment as a sorting means a commercially available sorting apparatus is configured to run according to said method or is based on a commercial apparatus or comprises such a commercial machine. In one embodiment the said adaption is the equipment of the sorting means with an NIR-sensor. Examples for such commercially available sorting machines are IXeed™ produced by IMIX Vision Support Systems B.V., the sorting machines produced by BEST NV, SORTEX© produced by Bühler GmbH, the sorting machines produced by Satake LTD. and the agricultural processing machines produced by Fowler Westrup (India) pvt. LTD.

The present invention also relates to purified and/or sorted fractions of seeds, e.g. sugar beet seeds, characterized in that at least 50%, at least 60%, at least 70%, at least 80%, at least 85%, at least 90%, at least 95%, at least 99%, and up to 60%, up to 70%, up to 80%, up to 90%, up to 100% of the sugar beet seed within said fraction exhibit a certain quality of composition.

In one embodiment said sorted fraction of seeds, e.g. sugar beet seeds, is obtained by one or more of the methods discussed above and/or by the use of one or more of the sorting means discussed above.

In one embodiment the sorted fraction of the seeds, e.g. sugar beet seeds, shows one or more improved field emergence characteristics in comparison to unsorted sugar-beet seed before the sorting process. In yet another embodiment the sorted fraction comprising more than 50%, more than 60%, more than 70%, more than 80%, more than 85%, more than 90%, more than 95%, more than 96%, more than 97%, more than 98%, more than 99% of seeds belonging to the class "no free space" and/or "free space 1", in one embodiment measured with 2D-X-ray, in another embodiment measured with 3D-CT.

In one embodiment the sorted fraction of sugar beet seeds comprises more than 50%, more than 60%, more than 70%, more than 80%, more than 85%, more than 90%, more than 95%, more than 99% of seeds with more than 75%, more than 85%, more than 95% filling degree.

In another aspect the method further comprises a step of combining two or more sorted fractions of seeds. This embodiment is particularly useful for providing seeds having a tailor-made distribution of certain fractions in certain, freely selectable amounts. In one embodiment said fractions are combined to produce a certain ratio between seeds of the first fraction and seeds of at least one further fraction. For example, tailor-made seed lots can be produced which consist of 95% of seeds of one fraction combined with 5% of seeds of another fraction.

This invention also relates to a computer program product comprising a program code saved on a machine readable carrier, which executes one of the methods mentioned above if running in a sorting means as mentioned above.

The term "day degree" used within this application refers to the integral of a function of time that generally varies with temperature. In one embodiment the function may be truncated to upper and lower limits that vary by organism, or to limits that are appropriate for climate control. In one embodiment the function may be estimated or measured as reference to a chosen base temperature. The temperature is measured in the soil to get the actual temperature that the seed experiences.

In one embodiment, in case of sugar beet seeds the "day degree" may be computed as the sum of all modified mean temperatures of each day, wherein the "modified mean temperature" is the mean temperature of each day minus 3. For example assuming that the mean temperature for day 1 is 5° C., the mean temperature of day 2 is 10° C. and the mean temperature of day 3 is 15° C., the "day degree" is then computed as (5−3)+(10−3)+(15−3)=2+7+12=21 day degrees. During the time the temperature is below 3 degrees, nothing is added to or subtracted from the day degrees.

In another embodiment the "day degree" may be computed partially, e.g. if the temperature is 15° C., it is calculated as (15−3)/24=0.5 "day degrees" per hour. In one embodiment the "day degree" may be computed according to the following formula $$\text{day degree} = \sum_{n=1}^{N} (T_n - C_{mod}),$$

wherein during the time the temperature is below $C_{mod}$ nothing is added or subtracted from the day degrees. $C_{mod}$ may be chosen according to the seed measured, in particular $C_{mod}$ may be chosen according to the temperature below which the seed stays dormant. In case of sugar-beet seeds in one embodiment $C_{mod}$ is 3. The term "day" herein refers to a period of 24 hours.

SHORT DESCRIPTION OF THE FIGURES

FIG. 1 shows the field emergence characteristics of different sugar beet seed classes according to their "free space part" used for an embodiment of the method for classifying seeds according to the invention. The y-axis describes the percentage of seeds showing field emergence. The x-axis refers to "day degree" which is computed as the integral of a function of time that generally varies with temperature as explained elsewhere. In FIG. 1 the "day degree" for sugar beets was computed as the sum of all mean temperatures of all days minus 3. Between 80 and 120 day degrees a clear split between the different free space classes in respect to their field emergence can be observed. After 120 day degrees about 90% of the seeds belonging to the no free space and free space 1 class have shown field emergence, the field emergence of seeds belonging to the class of free space 2 is at about 80% and only below 60% of seeds belonging to the class of free space 3 have shown field emergence.

Figure 8:
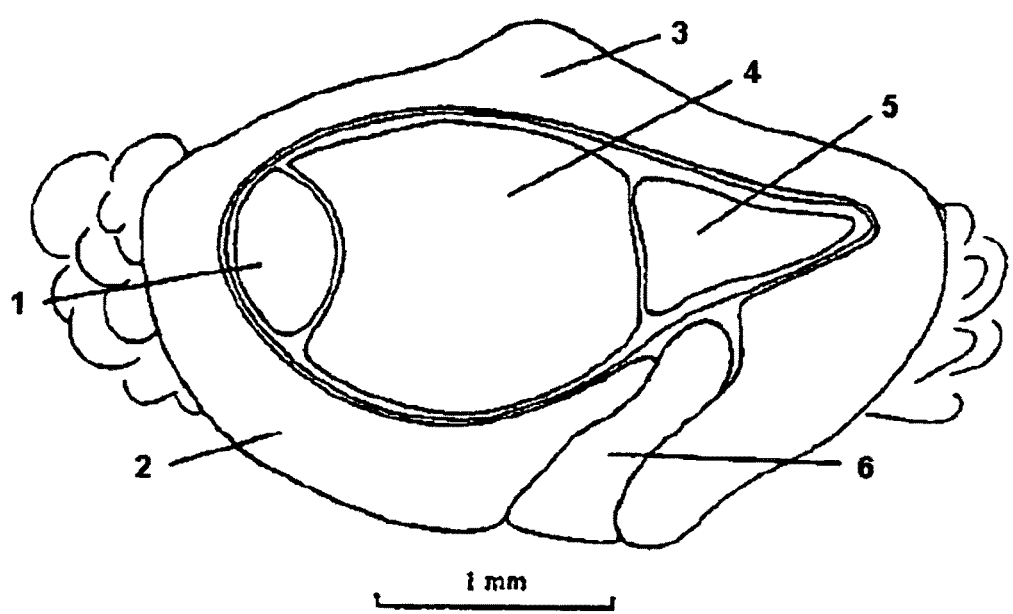

FIG. 8 depicts a diagram of a transverse section of a monogerm seed (PERRY, D. A. & HARRISON, J. G., (1974). Studies on the sensitivity of monogerm sugar beet germination to water. Ann. Appl. Biol. 77, 51-60). The plumule (1), fruit wall (2), fruit cap (i.e., operculum) (3), perisperm (4), radicle (5) and basal pore (6) are shown.

DETAILED DESCRIPTION OF THE INVENTION

The present invention utilizes the surprising finding that a heterogeneous accumulation of seeds, in particular sugar beet seeds, can be classified by infrared spectroscopy, in particular near-infrared spectroscopy according to their functional quality of field emergence characteristics. This classification allows the individual classification of viable seeds according to their functional quality of field emergence characteristics or to their structural quality of free space present in the seed, which surprisingly is correlated with the functional quality of field emergence.

In one embodiment the present invention utilizes the surprising finding that the structural quality of seeds, in particular sugar beet seeds, called "free space" as defined elsewhere in this application is correlated with the functional quality of said seeds called "field emergence". In a further embodiment the present invention utilizes the surprising finding that the structural quality of "free space" can be a measured by IR-spectroscopy, in particular NIR-spectroscopy. In one further embodiment a measurement with IR-spectroscopy, in particular NIR-spectroscopy, is used to classify and/or sort seeds, in particular sugar beet seeds, according to their "free space" class. In yet another embodiment said correlation between "free space" and "field emergence" is utilized to classify and/or sort seeds, in particular sugar beet seeds, according to their "field emergence" class with IR-spectroscopy, in particular NIR-spectroscopy.

The present invention further relates to the use of a learning algorithm, in particular a support vector machine, to differentiate the measured IR-spectra, in particular NIR-spectra, and accordingly sort the respective seeds into different qualities of seed populations.

The present invention further relates to the usage of seed sorting machines for the production of a new seed population, wherein one or more qualities of the seed population, such as field emergence characteristics, are improved in comparison to the unsorted and/or native occurring seed population.

Furthermore, the invention relates also to sorted fractions of seeds, which are produced by the method of the invention and comprise improved qualities of the seed population in comparison to the unsorted and/or native occurring seed population.

Thus, the present invention encompasses a method for sorting seeds, comprising the steps of measuring the IR-spectrum of each seed, classifying each seed according to its IR-spectrum, and optionally sorting each seed according to said classification in different fractions of seeds, wherein each fraction of seeds reflects one seed-class differing from the other seed-classes by a quality of composition, wherein said quality of composition is reflected in a specific IR-spectrum.

1. Infrared Spectroscopy and Near-Infrared Spectroscopy

Within this invention infrared spectroscopy may be used to evaluate the quality of the composition of the seeds. Infrared spectroscopy examines absorption and transmission of photons in the infrared energy range, based on their frequency and intensity.

Different IR-spectra are measured depending on the type of IR used. Within this application the IR-spectra are divided in:

Far-infrared, ranging from a frequency of 300 GHz and/or a wavelength of 1 mm to a frequency of 30 THz and/or 10 μm wavelength. The lower part of this range may also be called microwaves. This radiation is typically absorbed by so-called rotational modes in gas-phase molecules, by molecular motions in liquids, and by phonons in solids.

Mid-infrared, from frequencies of 30 to 120 THz and/or wavelengths of 10 to 2.7 μm. Hot objects (black-body radiators) can radiate strongly in this range. It is absorbed by molecular vibrations, where the different atoms in a molecule vibrate around their equilibrium positions.

Near-infrared, from frequencies of 120 to 400 THz and/or wavelengths of 2,700 to 750 nm. Physical processes that are relevant for this range are similar to those for visible light. Near-infrared spectroscopy is based on molecular overtone and combination vibrations. Such transitions are forbidden by the selection rules of quantum mechanics. As a result, the molar absorptivity in the NIR region is typically quite small. One advantage is that NIR can typically penetrate much farther into a sample than mid-infrared radiation. Near-infrared spectroscopy is, therefore, very useful in probing material with little or no sample preparation.

It is one of the important findings within this invention, that IR-spectra, in particular NIR-spectra, can not only be used to identify single chemical characteristics of a certain chemical group, like water or sugar content, but are also suitable to define more complex characteristics, such as chemical and/or structural and/or sensoric and/or functional qualities, in particular qualities associated with the field emergence properties of different seeds. In one embodiment, said IR-spectra, in particular NIR-spectra, are used to define the free space of different seeds associated with the field emergence property of the seeds.

Instrumentation for near-infrared spectroscopy is similar to instruments for the visible and mid-infrared ranges. There is a source, a detector, and a dispersive element (such as a prism or, more common, a diffraction grating) to allow the intensity at different wavelengths to be recorded. Fourier NIR instruments using an interferometer are also common, especially for wavelengths above ~1,000 nm.

Depending on the sample, the spectrum may be measured in either reflection or transmission.

The IR-spectra may be filtered, in some embodiments also called "pre-treatment", before statistical analysis. In one embodiment the spectra are filtered with a derivative of the spectra. In one embodiment a multiplicative scattering correction (MSC) may be used for pre-treatment.

In another embodiment the 1st, 2nd, 3rd, 4th or 5th derivative is calculated. In one embodiment these derivatives are filtered with different filter-algorithms. In one embodiment a smoothing filter was applied. In one embodiment the $2^{nd}$ derivative using a Savitzky-Golay smoothing filter with the number of smoothing points set between 10 to 50, in another embodiment smoothing points set between 15 to 40, in another embodiment smoothing points set between 20 to 30, in one embodiment smoothing points set to 21 are applied.

The Savitzky-Golay smoothing filter is a type of filter first described in 1964 by Abraham Savitzky and Marcel J. E. Golay (Savitzky, A.; Golay, M. J. E. (1964). "Smoothing and Differentiation of Data by Simplified Least Squares Procedures". Analytical Chemistry 36 (8): 1627-1639) which is incorporated by reference herein.

The Savitzky-Golay method essentially performs a local polynomial regression (of degree k) on a series of values (of at least k+1 points which are treated as being equally spaced in the series) to determine the smoothed value for each point. Methods are also provided for calculating the first up to the fifth derivatives.

The main advantage of this approach is that it preserves features of the distribution such as relative maxima, minima and width, which are usually 'flattened' by other adjacent averaging techniques (like moving averages, for example).

Please note that Savitzky and Golay's original paper contained several typographical errors that were subsequently corrected by Steinier, Termonia, and Deltour (Analytical Chemistry 44 (11): 1906-1909) which is incorporated by reference herein.

2. Classification

To establish a classification scheme, it may be appropriate to create a "training seed" set, which can be used as a standard. In one embodiment the classification applied to the training seed set is the same classification applied later to the unsorted seeds during a classification and/or sorting method according to the present invention. In one embodiment the training seed set is used to create a classification scheme, which then can be used to classify unknown IR-spectra into the classes defined by the training seeds. In one embodiment this is done by comparing the IR-spectrum of a unknown seed with the IR-spectra classes defined with the training seed. In another embodiment the IR-spectra may be classified de novo, that is without using a training seed set for calibration. In one embodiment, the IR-spectra of unknown seeds is classified using a self-learning algorithm, in particular a support vector machine. In some embodiments the "training seeds" may be created by X-ray or three-dimensional computer tomography (CT) analysis as outlined below.

In one embodiment the seeds, e.g. sugar-beet seeds, are classified and/or sorted according to their quality of composition. Said quality of composition is selected from the group consisting of a chemical quality, a structural quality, a sensoric quality or a functional quality or a combination of one or more thereof.

Thus, in one embodiment the seeds are divided in two classes, one having the desired seed quality/qualities and one class for the seeds not fulfilling said quality criteria.

In another embodiment the seeds are divided into more than two, more than three, more than four and up to five, up to six, up to seven, up to eight, up to nine and up to ten classes, thereby differentiating the seeds more precisely from each other by selecting for different quality criteria.

In one embodiment a "training seed" set, in particular a "training seed" set of sugar beet seeds, is produced according to its structural quality of "free space". In another embodiment the structural quality of "free space" is used for classification of a training seed set as well as an unsorted seed set. In yet a further embodiment only an unsorted seed set is classified according to the structural quality of "free space" without the use of a training seed set.

The definition of the "free space" refers to or is a measure for or is correlated to the volume inside a seed, which is not occupied by solid and/or liquid matter, i.e., is occupied by, for example, gas. Such volume can be coherent or split or separated to other volumes inside the seed. In one embodiment the feature "free space" is a space within the seed which is not filled by the embryo. In one embodiment the "free space" is described by the percentage of true seed volume to fruit wall cavity volume.

In one embodiment a three-dimensional computer tomograph (3D-CT) may be used for characterization of sugar beet seed according to the approach published by Maisl et al., "Process Monitoring using three dimensional Computed Tomography and Automatic Image Processing", Deutsche Gesellschaft für Zerstörungsfreie Prüfung e.V.-DGZfP-, Berlin; European Federation for Non-Destructive Testing—EFNDT—: 9th European Conference on NDT. ECNDT Berlin 2006. CD-ROM: Sep. 25 to 29, 2006; Berlin: DGZfP, 2006 (DGZfP Proceedings BB 103-CD) ISBN: 3-931381-86-2; pp. We.3.7.1. (available under http://publica.fraunhofer.de/documents/N-50556.html), which are incorporated by reference herein.

In one embodiment the "filling degree" of the seed may be used to define the "free space". It is computed as "the true seed part/fruit wall cavity part". For example if the true seed part is 30% of the total seed volume and the fruit wall cavity part is 40% of the total seed volume a filling degree of 30/40=0.75 or 75% can be computed.

In one embodiment the "filling degree" categories mentioned herein are measured via automated characterization of singularized sugar beet seeds by means of three-dimensional computer-tomography and image processing.

Figure 1:
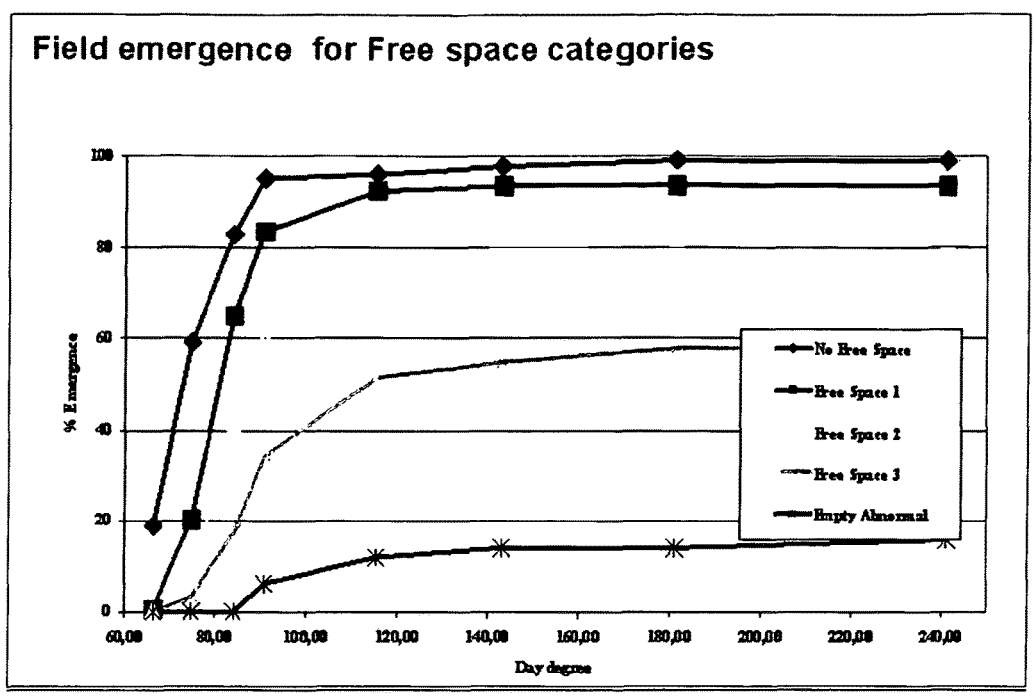

The "filling degree" and/or "free space" may be measured in plant seeds. In one embodiment "filling degree" and/or "free space" is measured in seeds of agricultural crop plants For purpose of classification and sorting the following "free space"-classes are used within this invention:

The "no free space" class (NFS) describes seeds which show the best field emergence characteristics. This class of seeds is characterized by a very small or no free space(s) within the seed. For example, seeds of the "no free space" class have a filling degree of at least 95%, at least 96%, at least 97%, at least 98%, at least 99% and up to 96%, up to 97%, up to 98%, up to 99%, up to 100%, when evaluated by 3D-CT. These seeds are considered the best quality class of seeds, since for example, they show the best field emergence characteristics (cf. FIG. 1).

The "free space 1" class (FS1) describes seeds with a small free space. For example seeds of the "free space 1" class have a filling degree of at least 85%, at least 86%, at least 87%, at least 88%, at least 89%, at least 90%, at least 91%, at least 92%, at least 93%, at least 94% and up to 86%, up to 87%, up to 88%, up to 89%, up to 90%, up to 91%, up to 92%, up to 93%, up to 94%, up to 94.9% when evaluated by 3D-CT. Seeds of this class show a slight diminished field emergence characteristic as compared to "no free space" seeds. In terms of seed quality such seeds show, for example, a reduction of maximal 10% in field emergence characteristics as compared to the "no free space" class seeds (cf. FIG. 1).

The "free space 2" class (FS2) describes seeds with a mid-sized free space. For example seeds of the "free space 2" class have a filling degree of at least 75%, at least 76%, at least 77%, at least 78%, at least 79%, at least 80%, at least 81%, at least 82%, at least 83%, at least 84% and up to 76%, up to 77%, up to 78%, up to 79%, up to 80%, up to 81%, up to 82%, up to 83%, up to 84%, up to 84.9% when evaluated by 3D-CT. Such seeds show, for example, a reduction of about 20% in field emergence characteristics as compared to the "no free space" class seeds (cf. FIG. 1).

The "free space 3" class (FS3) describes seeds with a quite big free space, i.e., these seeds are poorly filled. For example, the filling degree of "free space 3" class seed is between at least 30%, at least 40%, at least 50% and up to 60%, up to 65%, up to 70%, up to 74.9%. Such seeds show, for example, a reduction of about 40-50% in field emergence characteristics as compared to the "no free space" class seeds (cf. FIG. 1).

Thus, the "free space" classification may be used to discriminate between the quality of field emergence characteristics in seeds which are all per se viable. Accordingly, it may be used to discriminate between different subsets of viable seeds, rather than to discriminate between dead or viable seeds.

Thus, in some embodiments different categories of viable sugar beet seeds are classified and sorted according to their "free space" classification, creating two or more subsets of viable sugar beet seeds.

Therein for example a first viable sugar beet seeds subset comprises sugar beets seeds of the "no free space" class resulting in the "quality of composition" of desirable field emergence characteristics, i.e. with desirable viability and/or desirable growth-speed and/or desirable vigour.

The second viable sugar beet seeds subset comprises sugar beets seeds of "free space 1" class resulting in the "quality of composition" of the field emergence of said sugar beet seeds with 1%, 2%, 3%, 4%, 5%, 6%, 7%, 8%, 9% and up to 10% reduced field emergence as compared to the first subset, i.e. with 1%, 2%, 3%, 4%, 5%, 6%, 7%, 8%, 9% and up to 10% reduced viability and/or 1%, 2%, 3%, 4%, 5%, 6%, 7%, 8%, 9% and up to 10% reduced growth-speed and/or 1%, 2%, 3%, 4%, 5%, 6%, 7%, 8%, 9% and up to 10% reduced vigour.

The third viable sugar beet seeds subset comprises sugar beets seeds of "free space 2" class resulting in the "quality of composition" of the field emergence of said sugar beet seeds with 11%, 12%, 13%, 14%, 15%, 16%, 17%, 18%, 19% and up to 20% reduced field emergence as compared to the first subset, i.e. with 11%, 12%, 13%, 14%, 15%, 16%, 17%, 18%, 19% and up to 20% reduced viability and/or 11%, 12%, 13%, 14%, 15%, 16%, 17%, 18%, 19% and up to 20% reduced growth-speed and/or 11%, 12%, 13%, 14%, 15%, 16%, 17%, 18%, 19% and up to 20% reduced vigour.

The fourth viable sugar beet seeds subset comprises sugar beets seeds of "free space 3" class resulting in the "quality of composition" of the field emergence of said sugar beet seeds with 20%, 30%, 40% and up to 50% reduced field emergence as compared to the first subset, i.e. with 20%, 30%, 40% and up to 50% reduced viability and/or 20%, 30%, 40% and up to 50% reduced growth-speed and/or 20%, 30%, 40% and up to 50% reduced vigour.

Seeds in which no or just a partial embryo is present, are called "empty" (E) or "partially empty" (PE), respectively. For example the filling degree of "empty" or "partially empty" class seed is below a filling degree of 30%. Seeds with two embryos in one seed are called "twins" (TW). These classes are considered the least desirable classes since seeds of these classes tend to no field emergence at all (cf. FIG. 1).

Thus, in one embodiment a "training seed" set is created by sorting seeds which possess a filling degree of 85%. This results in a "training seed" set which possesses primarily "no free space" and "free-space 1" seeds.

In another embodiment also seeds with "free space 2" are included into the "training seed" set. In this case the "cut-off" is set to a filling degree of 75%. In a further embodiment, a "training seed" set for each category is produced. Thus, ranges of for example 100 to 95% filling degree for "no free space" seeds, 94.9 to 85% filling degree for "free-space 1" seeds and 84.9 to 75% filling degree for "free-space 2" seeds etc. is chosen.

In some embodiments, a classifying and/or sorting may be directed to the differentiation between NFS and FS1 only on one hand and FS2, FS3, and the other seed classes on the other hand. However, in other embodiments a classification for 3, 4, 5, 6, 7, 8, 9 or 10 different classes is applied. Furthermore, since the field emergence performance of FS2-seeds is still considered tolerable (cf. FIG. 1), in one embodiment a classification and/or sorting is directed to isolate NFS, FS1 and FS2 as desirable seeds fractions.

In one embodiment a classification results in sugar beet seeds falling in the categories "no free space" (NFS) with 95% to 100% filling degree, "free space 1" (FS1) with 85% to 94.9% filling degree, "free space 2" (FS2) with 75% to 84.9% filling degree and "free space 3" (FS3) with 30% to 74.9% filling degree. Classes with less filling degree are non-desired classes and may be called in some embodiments "empty abnormal" and "empty".

In another embodiment the correct sorting of the seeds is verified by applying non-destructive and/or destructive analysis methods to each seed class and/or a control sample after the sorting. Such "destructive analysis methods" are e.g. the separation and/or slicing of the seeds or usage of the seeds in field trials.

The result of the analysis may be fed back into the classification procedure to improve the classification process.

The flow-charts (FIGS. 4, 5, 6 and 7) further exemplify preferred embodiments of the classification and or sorting process of the present invention:

In one embodiment (FIG. 4) a fraction of "training seeds" (1) contains between 10-1000 seeds and is used to calibrate the automated classification system. The training seeds (1) are analysed with an IR-spectrometer (2), in particular a NIR-spectrometer. Optionally the measured spectra are then filtered (3), in particular with a smoothing filter after application of the 2nd derivative on the spectrum. This information is then fed to a means (4) able to classify the IR-spectra, in particular a computer running for example a support vector machine. The information gained during classification may be optionally fed back to the classification means (4) via a self-learning process (8), and/or may be optionally used to improve the filtering (7) and/or may be optionally used to improve the IR-spectroscopy (6). The process then results in a classification scheme (5), which may be used in a sorting means (11) or other processes (9).

In one embodiment the NIR-spectrum measurement is improved by a feed-back mechanism (6), (7) and/or (8). NIR analysis relies on developing a calibration model (Y=FX) that relates the NIR spectra (Y matrix) of the calibration set of samples, as response blocks, to their known chemical property (X matrix) as predictor block, where F can be any mathematical function. This model is validated by cross validation method and/or the new external validation sample set and then used to predict the quality of further samples based on their NIR spectra.

In one embodiment the "feed-back" steps outlined above aim for the selection of ranges of IR-spectra which comprise the most differentiating information. Thus, IR-ranges with quite similar information throughout the different seed classes are to be avoided. Thus, also iterative processes may be applied, narrowing down the IR-spectra with the highest "information-content", for example, by using seed-classes of earlier sorting procedures as training seeds. Thus, in some embodiments a sorting cascade is applied comprising steps of an initial "rough sorting" and further steps of "fine-sorting", where in the "rough-sorting" process the classification is done using the full NIR-spectrum range, whereas in the "fine-sorting" process certain selected spectral regions and/or single peaks are chosen for classification. As such for example very different seed classes may be sorted first in the "rough-sorting" process, whereas during the "fine-sorting" process related classes with small differences may be differentiated.

In another embodiment (FIG. 5) the sorting means (11) may be used to sort parts or all of the training seeds (1) by using the classification scheme (5), thereby producing sorted fractions of seeds (12, 13, 14). The quality of the sorted seeds may be analysed with non-destructive and/or destructive methods (15) and the result may be optionally used to further improve the set-up of the classification means (4) (10,8), and/or filter (3) (10,7) and/or IR-spectrometer (2) (10,6). Again the process results in a classification scheme (5), which may be used in a sorting means (11) or other processes (9).

In another embodiment (FIG. 6) the training seeds (1) are pre-sorted by hand or automated devices using e.g. 2D-X-ray and/or 3D-CT as described elsewhere. Thereby different training seed classes (1a, 1b, 1c) are produced. The seeds are then measured independently for each class as described above. However, in addition to the already described improvement steps (6,7,8) also the automated classification of the seeds is compared to the expected sorting (16) and the results are used to further improve the set-up of the classification means (4) (17,8), and/or filter (3) (17,7) and/or IR-spectrometer (2) (17,6). Again the process results in a classification scheme (5), which may be used in a sorting means (11) or other processes (9).

In another embodiment (FIG. 7) unsorted seeds (18) are measured with an IR-spectrometer (2). These IR-spectra may be optionally filtered (3). A comparison means (19), in particular a computer, compares the IR-spectra obtained with a classification scheme (9) which is for example derived from training processes as described above, in particular it is the same classification scheme like (5). The result of the classification is fed into a sorting means (11) which then sorts the unsorted seeds (18) according to their classification, thereby producing fractions of sorted seeds (20, 21, 22) according to their quality class.

In further embodiments the depicted steps may be also combined, for example, if more improvement of classification quality is needed or the training and the sorting process is to be performed in one procedure.

3. Statistical Analysis of NIR-Spectra and Classification of Sugar-Beet Seeds

In one embodiment the classification of the sugar beet seed is performed by directly evaluating the NIR-spectra with respect to unique peak characteristics of the different seed classes. Such an evaluation may be focus on one, two, three, four, five and up to several 100 different peaks or other spectra-characteristics like zero point(s), low and high point(s), inflection point(s) and/or any other characteristic pattern which is suitable to divide one or more spectra of different seed classes from each other. In some cases also different peak-amplitudes may be sufficient to divide between the spectra of different seed classes. Further, the ratio of amplitudes of specific peaks in the spectra of different seed classes may be sufficient to divide between the spectra of different seed classes.

For classification of such complex data in general the following methods may be applicable: discriminant PLS (PLS-DA), Fischer discrimination, k nearest neighbours (kNN), artificial neural networks, SIMCA and/or support vector machines (SVM). In one embodiment SVM is used.

In another embodiment the whole NIR spectrum is used to form multiple variables where e.g. one variable comprises every second wavelength resulting in totally more than 1,000 variables in each spectrum. Such huge amount of data cannot be easily be handled by classic statistical methods, instead by using partial least square (PLS) regression method the vast number of variables will be reduced to a few orthogonal principle components.

For further reference of the PLS-algorithm please be referred to Haenlein, M., Kaplan, A. M.: A beginner's guide to partial least squares (PLS) analysis. In: Understanding Statistics. 3, Nr. 4, 2004, S. 283-297.

In one embodiment, another approach also using the whole IR-spectrum is applied which is the use of so-called "support vector machines" (SVM). SVM is a new technique for a discriminating analysis on IR-spectral data.

Support vector machines (SVMs) are a set of related supervised learning methods which analyze data and recognize patterns and are used for statistical classification and regression analysis. An SVM training algorithm builds a model that predicts whether a new example falls into one category or the other when given a set of training examples, each marked as belonging to one of two categories. Intuitively, an SVM model is a representation of the examples as points in space, mapped so that the examples of the separate categories are divided by a clear gap that is as wide as possible. New examples are then mapped into that same space and predicted to belong to a category based on which side of the gap they fall on.

For further reference of the SVM-algorithm be referred to Vladimir Vapnik "The Nature of Statistical Learning Theory", Springer Verlag, 1995, ISBN 0-387-98780-0 and Vladimir Vapnik, et al., "Estimation of Dependences Based on Empirical Data", Springer Verlag, 2006, ISBN 0-387-308652, see especially appendix therefrom for recent developments, which are incorporated by reference herein.

SVMs are either implemented in certain mathematical and/or statistical programs or available as "stand-alone" programs. Examples for such SVMs are libSVM, RapidMiner (also known as YALE), SVMlight, Torch Machine, kernlab Machine (learning library in R with implemented SVM), Shogun Machine Learning Toolbox, Spider Machine Learning Toolbox, Lush, WEKA, or Shark.

For the invention any SVM is suitable as long as the percentage of falsely classified seeds when classifying the "training seed" is not higher than 10%, 20%, 30%, 40%, 50%.

In particular, settings resulting in less than 20%, less than 10%, less than 9%, less than 8%, less than 7%, less than 6%, less than 5%, less than 4%, less than 3%, less than 2%, less than 1% of false classified seeds are preferred.

4. Sorting of Seeds with a Seed Sorter

In one embodiment the classification scheme generated by the methods above is used to run a sorting means by having the classification scheme being implemented in the sorting means.

In one embodiment the sorting means comprises a control means, a sorting means and a sensoric means. The sorting means can be any means suitable to physically individualise the seeds according to their classification. The sensoric means may be a IR-sensor, in particular a NIR-sensor able to individually measure the NIR-spectrum of each seed.

The sorting apparatus is preferably configured to apply the method for classifying seeds according to the invention and/or the method for sorting seeds according to the invention. "Configured", in this context, means that the sorting apparatus hardware and/or software modification necessary in order to classify or sort, respectively, the seeds by using one of the methods according to the invention. For that purpose, the sorting apparatus preferably comprises at least one hardware component, e.g. a control means, which is specially configured to apply one of the methods described herein to classify or sort seeds.

Preferably, the sorting apparatus comprises a programmed electronic control means, e.g. a microcontroller, which is specially configured to apply one of the methods according the invention to classify or sort seeds or one of the preferred embodiments of the methods, respectively. For that purpose, the control means, preferably, comprises computing means, e.g. a computer or CPU, or other calculating means, and memory means. The memory means can comprise volatile memory means (e.g. types of RAM) and/or non-volatile memory means (e.g. types of ROM, e.g. EEPROM; e.g. firmware). The memory means, in particular the non-volatile memory means preferably comprises the computer program code, which is specially configured to apply one of the methods according the invention to classify or sort seeds or one of the preferred embodiments of the methods, respectively. However, other electronic circuit means can be used, which are specially configured to apply one of the methods according the invention to classify or sort seeds or one of the preferred embodiments of the methods, respectively.

Preferably, the electronic control means is configured to control other components of the sorting apparatus, e.g. the sorting means and the sensoric means in order to run a method according to the invention.

Preferably, the control means and/or said computer program code is/are configured to utilize the IR-spectra of the seeds for classifying and/or sorting seeds by using mathematical or statistical methods, e.g. said PLS and/or MSC and/or SVM method, thus implementing a method according to the invention.

In one embodiment the sorting means and/or the control means and/or the computer program code is/are configured to carry out the steps comprising individualizing sugar beet seeds, measuring the NIR-spectrum of each seed classifying each seed according to its specific NIR-spectrum related to a composition quality, in one embodiment according to a classification scheme produced elsewhere by methods disclosed herein, in another embodiment according to a classification scheme produced in the sorting means itself by methods disclosed herein, and sorting the seeds according to their classification in at least two different seed fractions, which optionally may be combined according to a mix ratio in the machine. In one embodiment of the present invention at least one of the sorted seed fractions is discarded or, optionally, destroyed within the machine.

In the preferred embodiment the hardware modification is in such a way to allow for the individual measurement and/or sorting of sugar beet seeds. In one embodiment the hardware modifications take for example into account and/or make use of the small size and/or the electrostatic features and/or the hygroscopic features of sugar beet seeds. In one embodiment, the hardware modifications comprise small indents in a surface small enough to just take one sugar beet seed per indent or electrostatically charged seeds or drying of seeds just before the sorting process or any combination thereof.

In one embodiment the control means or the computer of the sorter uses the information from the single seed NIR spectra and the classification methods disclosed above to divide the seeds in multi-fractions of seeds that have a similar, more homogeneous composition with respect to their filed emergence characteristics.

In one embodiment the hardware modification is in such a way that only a certain NIR-range is measured, for example wavelengths of 800 to 2700 nm, or 1000 to 2000 nm, or 1100 to 1500 nm, or 950 to 2040 nm, or 1060 to 2380 nm, or combinations thereof.

In one embodiment such a suitable seed sorter may be a NIR single seed sorter which comprises a rotating indented cylinder. The seeds in the indented pockets are inspected by the NIR sensor. The information is then fed to a computer and subsequently segregated to control at least 2 separated flows by pushing seeds into fractions by compressed air, which is configured to run a method according to the invention for controlling said machine.

In another embodiment a commercially available sorting machine is selected from the group comprising IXeed™ produced by IMIX Vision Support Systems B.V., the sorting machines produced by BEST NV, SORTEX© produced by Bühler GmbH, the sorting machines produced by Satake LTD. and the agricultural processing machines produced by Fowler Westrup (India) pvt. LTD. as already described above and is configured to perform the sorting steps outlined above, in particular by using said computer program code, which is configured to run a method according to the invention for controlling said machine.

Furthermore, in one embodiment the present invention also relates to sorted fractions of seeds, for example sugar beet seeds, characterized in that at least 50%, at least 60%, at least 70%, at least 80%, at least 85%, at least 90%, at least 95%, at least 99%, and up to 60%, up to 70%, up to 80%, up to 90%, up to 100% of the sugar beet seed within said fraction exhibit a certain quality of composition.

In one embodiment said sorted fraction of seeds, for example sugar beet seeds, is obtained by one or more of the methods mentioned above and/or by the use of one or more of the sorting means mentioned above.

In one embodiment the sorted fraction of the seeds, e.g. sugar beet seeds, shows one or more improved field emergence characteristics in comparison to unsorted sugar-beet seed before the sorting process. In yet another embodiment the sorted fraction comprising more than 50%, more than 60%, more than 70%, more than 80%, more than 90%, more than 95%, more than 99% of seeds with a filling degree of at least 75%, of at least 85%, of at least 95%, of at least 96%, of at least 97%, of at least 98%, of at least 99%.

EXAMPLES

The subject-matter of the invention is further exemplified by the following examples.

Example 1 shows the different field emergence characteristics of different "free space" seed classes.

Example 2 shows a classification of a fraction of sugar beet seeds depending on their NIR-spectra.

Example 1

A series of field trials was performed to evaluate the influence of seed-filling in sugar beet seeds on field emergence. The seeds were sorted with 2D-X-ray into different field space classes. Then the field emergence of the seeds was tested in field trials. The effect was substantial on field emergence. Seeds with little or no free space (i.e., NFS or FS1) showed a significant higher field emergence compared to classes with bigger free space (i.e., FS2, FS3) (cf. FIG. 1).

Example 2

To classify sugar beet seeds with NIR-spectroscopy and SVM-classification 142 sugar beet seeds were classified by X-ray in a first step and used as "training" samples, i.e., as seeds which could be used to calibrate the classification of sugar beet seeds with NIR-spectroscopy and to evaluate the sensitivity of the NIR-classification in the end.

Table 1 lists the number and abbreviations of the different seed-classes classified by X-ray as training samples.

TABLE 1

| Class | Number of seeds | Abbreviation |
| --- | --- | --- |
| FreeSpace 1 | 25 | FS1 |
| FreeSpace 2 | 25 | FS2 |
| FreeSpace 3/Empty Abnormal | 17 | FS3/EA |
| Part Empty Moon | 25 | PEM |
| Twin | 50 | Twin |

The free space classes indicates how well filled the seeds are. FS1, FS2, and FS3 are as described above. Twins are seeds which contain 2 embryos, which is not desirable since one seed only shall give one plant in the field. NIR-instrument used: Bruker Optics MPA (Multi Purpose Analyzer) with PbS detector.

The samples were measured by NIR in reflectance mode in range of wavenumbers 12500 to 3600 cm$^{-1}$, i.e., with wavelengths of 800 to 2700 nm.

Figure 2:
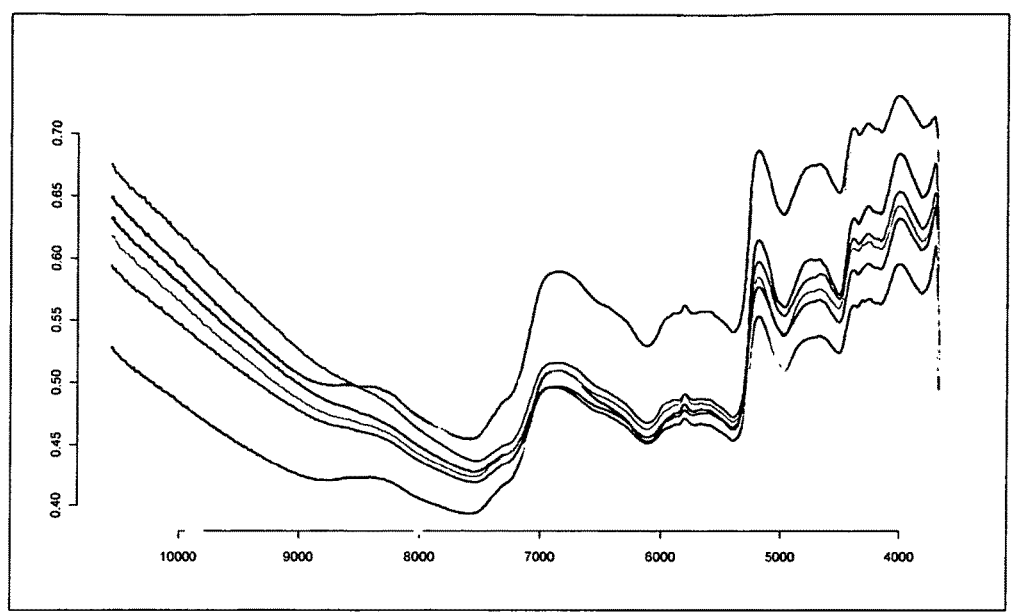
FIG. 2 shows examples of NIR-spectra from eight measured sugar beet seeds used for an embodiment of the method for classifying seeds according to the invention.
Figure 3:
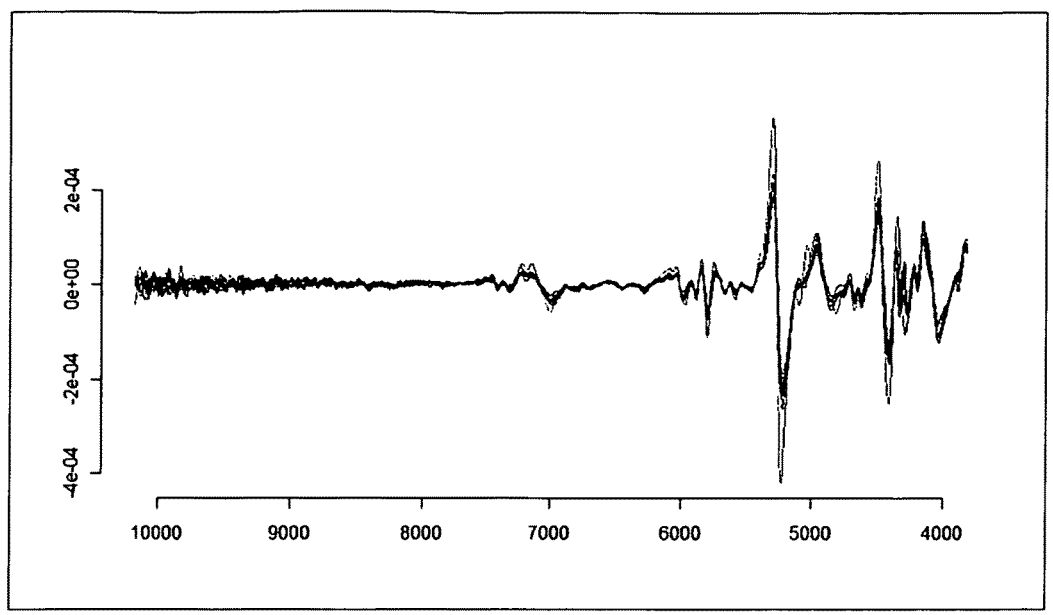
FIG. 3 shows the 2nd derivatives of the eight NIR-spectra of FIG. 2 used for an embodiment of the method for classifying seeds according to the invention.
Figure 4:
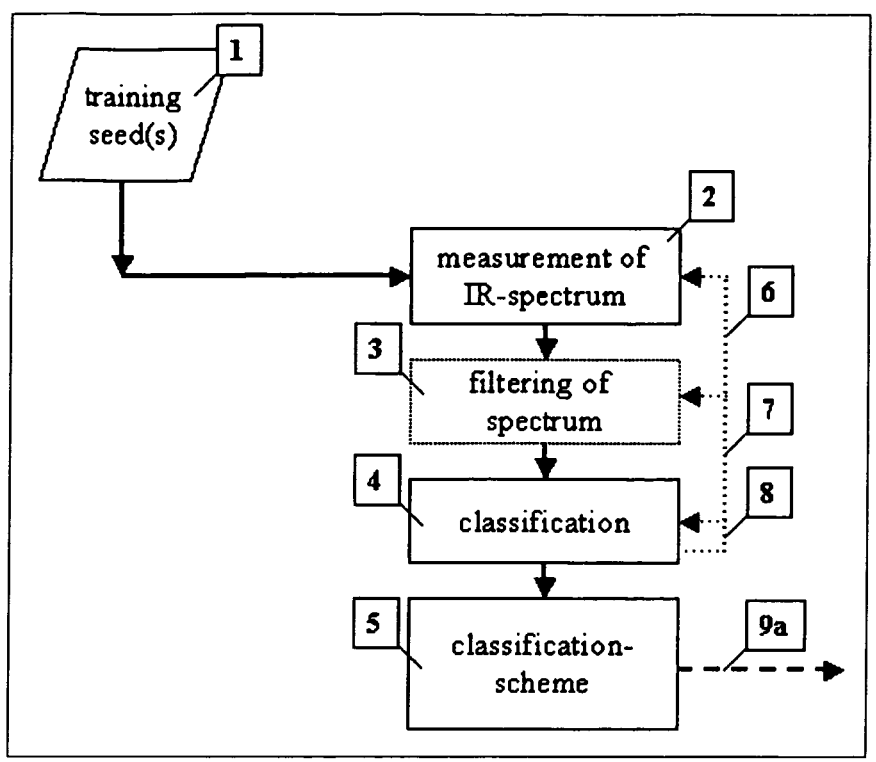
FIG. 4 shows a flow chart diagram depicting one possible training procedure for creating a classification scheme used for an embodiment of the method for classifying seeds according to the invention.
Figure 5:
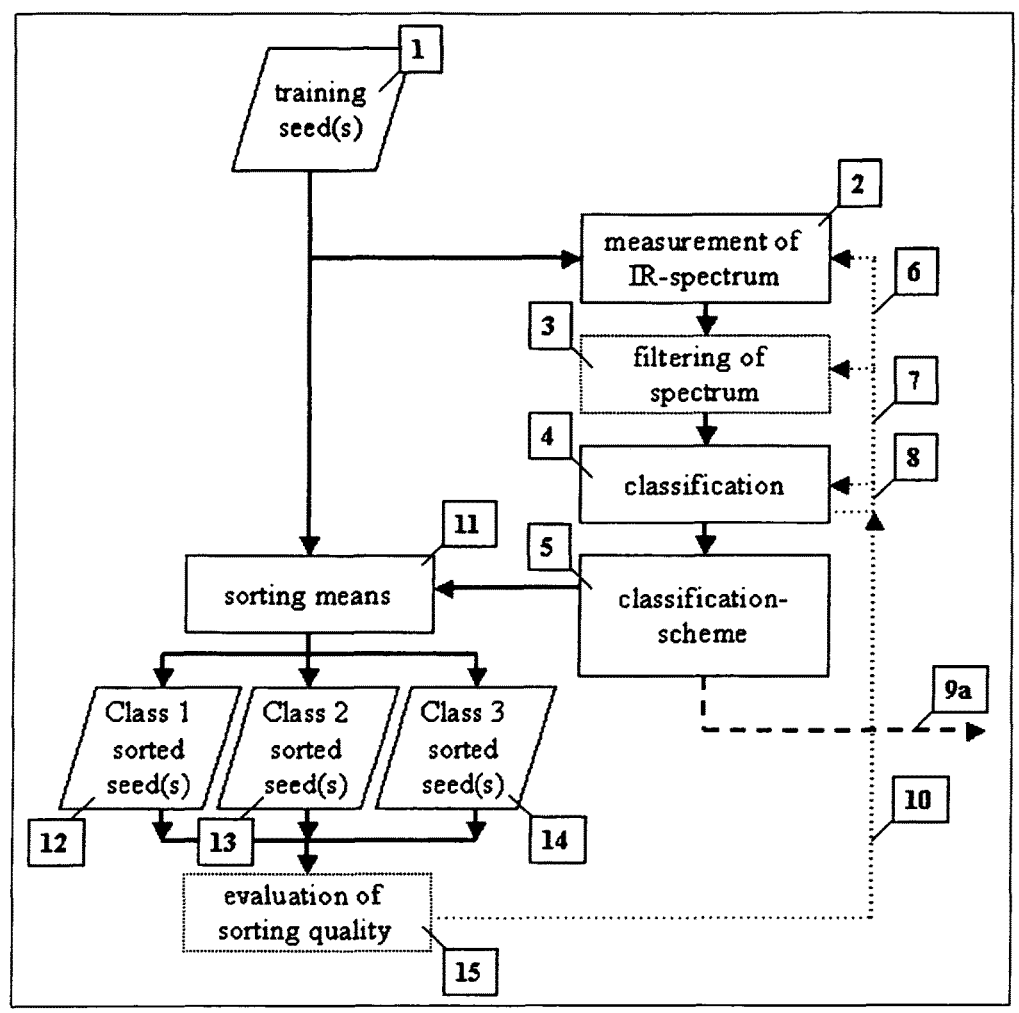
FIG. 5 shows a flow chart diagram depicting an alternative training and/or sorting procedure for creating a classification scheme and/or sorting used for an embodiment of the method for classifying seeds according to the invention.
Figure 6:
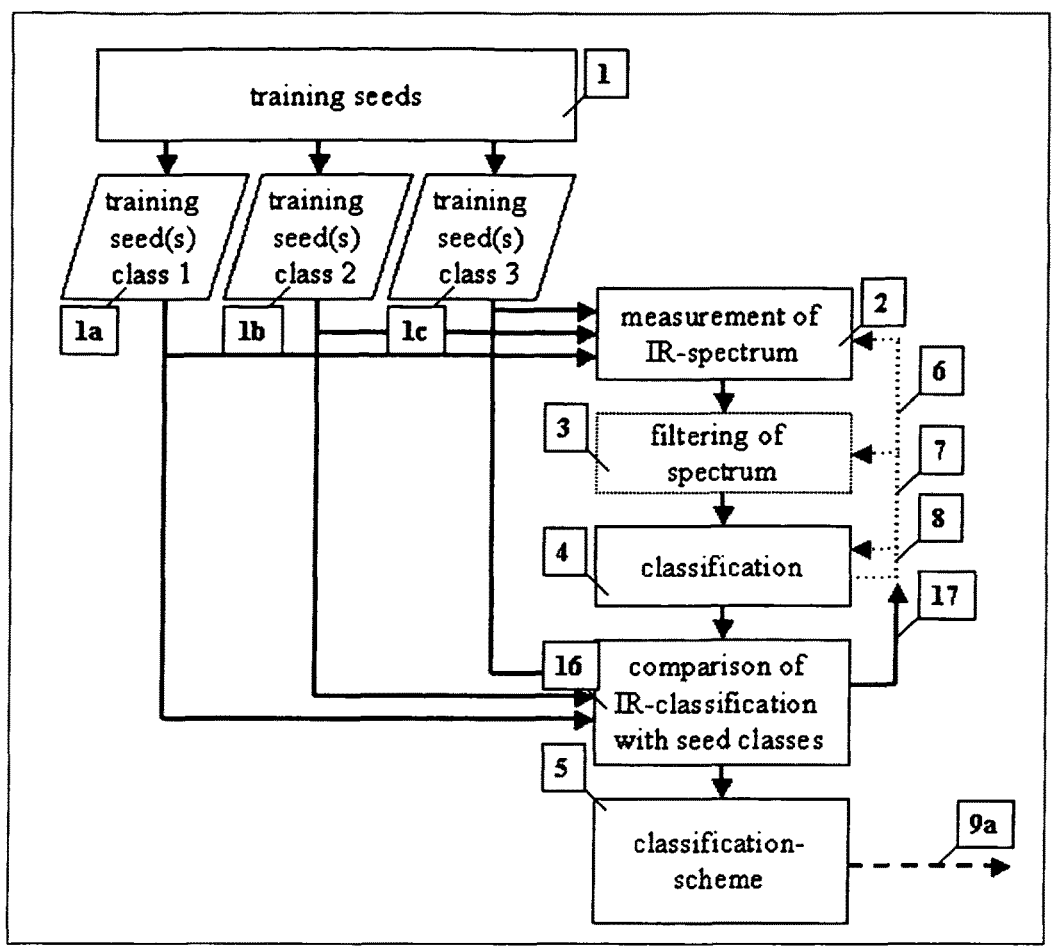
FIG. 6 shows a flow chart diagram depicting another alternative training procedure for creating a classification scheme used for an embodiment of the method for classifying seeds according to the invention.
Figure 7:
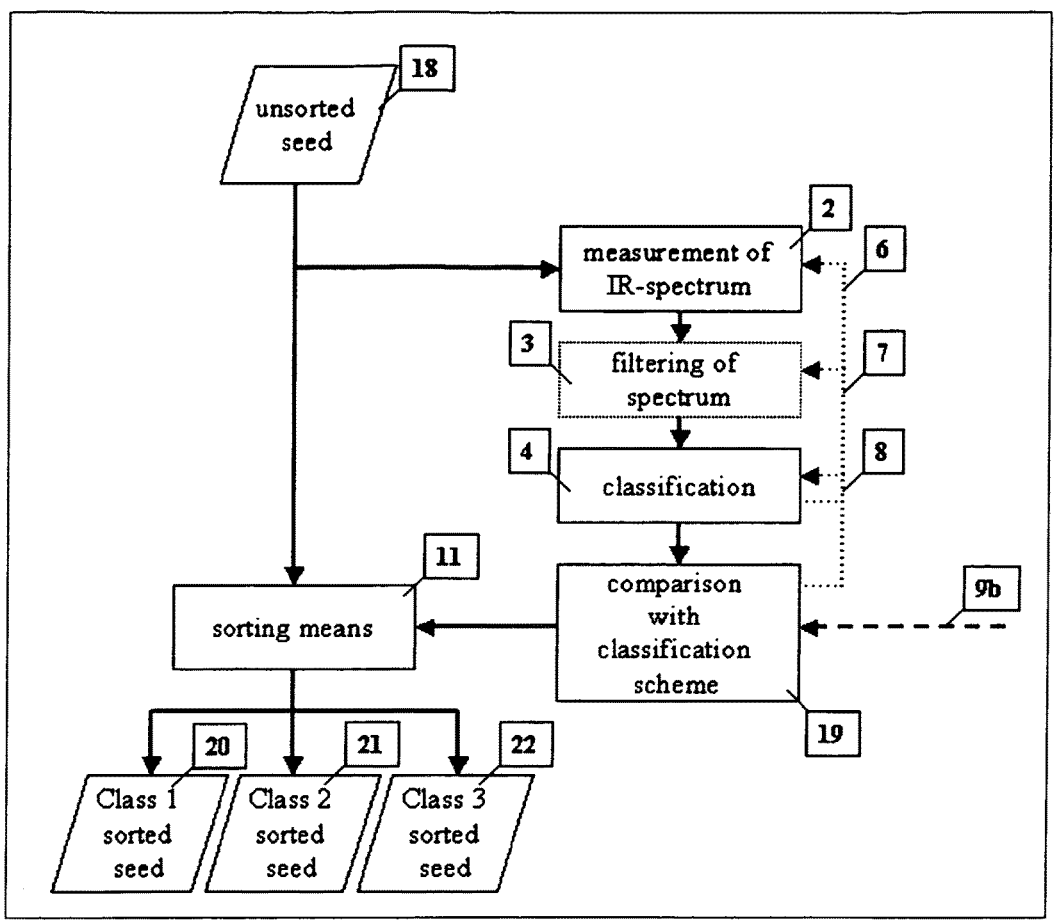
FIG. 7 shows a flow chart diagram depicting a possible sorting procedure used for an embodiment of the method for classifying seeds according to the invention.

All samples were measured in two ways, operculum down and operculum up, giving a total of 284 spectra to work with. FIG. 2 depicts NIR-spectra from eight of the measured seeds. Before classification the spectra where filtered with 2nd derivative using Savitzky-Golay smoothing filter with the number of smoothing points set to 21. FIG. 3 depicts the 2nd derivative of the NIR-spectra from eight of the measured seeds.

Classification of Seeds

For classification the SVM-algorithm was used from the package e1071 (http://crans-project.org/web/packages/e1071/index.html), a package for using SVM in the statistical computing language and environment R. The following parameters were applied in the program: svm.model<-svm (x=trainset, y=trainfactors, type="C-classification", kernel="radial", cost=100, gamma=0.00007), wherein x is the spectra for all samples in the trainset, y is the classes for all samples in the trainset, type is C-classification, kernel is radial, cost—100, gamma—0.00007.

The parameters adjusted to optimize classification were cost and gamma, the type and kernel stayed with "C-classification" and "radial", respectively, which were the default choice.

When determining the accuracy of classification the whole set of samples was randomly divided into a training-set containing two thirds of the sample and a test-set containing the remaining one third. A model was built with the training-set and tested on the test-set. This was done several times with new randomly selected test- and training-samples.

A classification of the samples when measuring seeds of all classes gave a correct class in 85% of the cases. This shows that the NIR clearly can discriminate between different free space classes determined by 2D-X-ray.

In table 2 the "predicted" seed classes measured by NIR-spectroscopy classified with the SVM-model vs. the "true" seed classes measured and classified by 2D-X-ray and image recognition for all five sugar beet seed classes are depicted. The numbers are in percent. For example 86% of FS1 has been correctly classified as FS1, 6% has been incorrectly classified as FS2, 1% as FS3-EA etc.

TABLE 2

|  |  | TRUE (2D X-ray Measurement) | | | | |
| --- | --- | --- | --- | --- | --- | --- |
|  |  | FS1 | FS2 | FS3 EA | PEM | Twin |
| PREDICTED (NIR-Prediction) | FS1 | 86 | 7 | 2 | 4 | 0 |
|  | FS2 | 6 | 79 | 8 | 9 | 2 |
|  | FS3 EA | 1 | 5 | 81 | 4 | 1 |
|  | PEM | 5 | 4 | 4 | 79 | 4 |
|  | Twin | 2 | 6 | 4 | 3 | 93 |

The result of 10 SVM-classification models as total percent of correctly classified sugar beet seeds is depicted in table 3.

TABLE 3

| Min | Mean | Max |
| --- | --- | --- |
| 81% | 85% | 88% |

The parameters chosen for the classification of the sugar beet seed into five classes are depicted in table 4.

TABLE 4

| Spectra | Spectrum range | Pretreatment | SVM-gamma | SVM-cost |
| --- | --- | --- | --- | --- |
| 284 | 10 500-4 900 cm−1 | 2nd derivative | 0.00007 | 100 |

Discrimination between sugar beet seeds of classes FS1, FS2 and Twin is depicted in table 5.

TABLE 5

|  |  | TRUE (2D- X-ray Measurement) | | |
| --- | --- | --- | --- | --- |
|  |  | FS1 | FS2 | Twin |
| PREDICTED (NIR-Prediction) | FS1 | 91 | 8 | 3 |
|  | FS2 | 6 | 89 | 5 |
|  | Twin | 3 | 2 | 92 |

The most important seeds to discriminate are FS2 and Twins. This is because they are the hardest to separate from the top quality FS1 seeds with normal separation methods.

The result of 10 SVM-classification models in total percent of correctly classified seeds is depicted in table 6.

TABLE 6

| Min | Mean | Max |
| --- | --- | --- |
| 86% | 91% | 94% |

Parameters for the classification of the sugar beet seeds from three different seed classes are depicted in table 7.

TABLE 7

| Samples | Spectrum range | Filtering | SVM-gamma | SVM-cost |
| --- | --- | --- | --- | --- |
| 150 | 9400-4200 cm−1 | 2nd derivative | 0.00007 | 1000 |

The invention claimed is:

1. A method for classifying sugar-beet seeds, comprising the steps of
    a. measuring an IR-spectrum of each seed,
    b. classifying seeds according to their IR-spectrum yielding at least two seed classes,
    c. sorting said classes of seeds yielding at least two sorted fractions of seeds which respectively differ from each other by a quality of composition, wherein said quality of composition is reflected in a specific IR-spectrum,
    wherein the sugar beet seed is classified according to one of the classes "no free space", "free space 1", "free space 2" and "free space 3" of the "free space" present in the sugar beet seed,
    wherein the first seed-class differs from the at least one other seed-class by a quality of composition,
    wherein the quality of composition is the functional quality of "field emergence characteristic" present in the sugar beet seed,
    wherein the quality of "field emergence characteristic" correlates with the quality of "free space" present in the sugar beet seed, and
    wherein said quality of composition is reflected in a specific IR-spectrum.

2. The method of claim 1, wherein the "field emergence characteristic" is defined as at least one of the characteristics selected from viability, growth-rate and vigour.

3. A method according to claim 1, wherein the quality of "field emergence characteristic" defines different subsets of viable seeds.

4. The method according to claim 1, wherein the IR-spectrum is either near infra-red (NIR), i.e., a frequency range from 120 to 400 THz and/or a wavelength of 2,700 to 750 nm, mid infra-red (MIR), i.e., a frequency range from 30 to 120 THz and/or a wavelength of 10 to 2.7 μm or far infra-red (FIR), i.e., a frequency range from 300 GHz to 30 THz and/or wavelength of 1 mm to 10 μm, or a combination of NIR, MIR and/or FIR.

5. A method of sorting sugar beet seeds, comprising the steps of
   a. measuring an IR-spectrum of each seed,
   b. classifying seeds according to their IR-spectrum yielding at least two seed classes,
   c. sorting said classes of seeds yielding at least two sorted fractions of seeds which respectively differ from each other by a quality of composition, wherein said quality of composition is reflected in a specific IR-spectrum,
wherein the IR-spectrum is either near infra-red (NIR), i.e., a frequency range from 120 to 400 THz and/or a wavelength of 2,700 to 750 nm, mid infra-red (MIR), i.e., a frequency range from 30 to 120 THz and/or a wavelength of 10 to 2.7 μm or far infra-red (FIR), i.e., a frequency range from 300 GHz to 30 THz and/or wavelength of 1 mm to 10 μm, or a combination of NIR, MIR and/or FIR,
wherein the quality of composition is the functional quality of "field emergence characteristic" present in the sugar beet seed,
wherein the "field emergence characteristic" is defined as at least one of the characteristics selected from viability, growth-rate and vigour,
wherein the quality of "field emergence characteristic" correlates with the quality of "free space" present in the sugar beet seed, and
wherein the sugar beet seed is classified according to one of the classes "no free space", "free space 1", "free space 2" and "free space 3" of the "free space" present in the sugar beet seed.

\* \* \* \* \*